United States Patent [19]

Millar

[11] Patent Number: 4,771,788

[45] Date of Patent: Sep. 20, 1988

[54] DOPPLER TIP WIRE GUIDE

[75] Inventor: Huntly D. Millar, Houston, Tex.

[73] Assignee: Pfizer Hospital Products Group, Inc., New York, N.Y.

[21] Appl. No.: 81,308

[22] Filed: Aug. 3, 1987

Related U.S. Application Data

[63] Continuation of Ser. No. 888,060, Jul. 18, 1986, abandoned.

[51] Int. Cl.$^4$ .............................................. A61B 10/00
[52] U.S. Cl. .......................... 128/661.09; 128/662.04; 128/662.06
[58] Field of Search ..................... 128/344, 348.1, 772, 128/660, 661, 663, 692, 642

[56] References Cited

U.S. PATENT DOCUMENTS

| | | | |
|---|---|---|---|
| 3,452,742 | 7/1969 | Muller | 128/772 |
| 3,521,620 | 7/1970 | Cook | 128/772 |
| 3,547,103 | 12/1970 | Cook | 128/772 |
| 3,817,089 | 6/1974 | Eggleton et al. | 128/661 |
| 3,827,115 | 8/1974 | Bom | 128/660 |
| 3,938,502 | 2/1976 | Bom | 128/661 |
| 3,995,623 | 12/1976 | Blake et al. | 128/642 |
| 4,112,773 | 9/1978 | Abts | 128/660 |
| 4,319,580 | 3/1982 | Colley et al. | 128/661 |
| 4,407,293 | 10/1983 | Suarez, Jr. et al. | 128/663 X |
| 4,534,363 | 8/1985 | Gold | 128/772 |
| 4,545,390 | 10/1985 | Leary | 128/344 X |
| 4,576,177 | 3/1986 | Webster, Jr. | 128/660 |
| 4,589,419 | 5/1986 | Laughlin et al. | 128/663 |

FOREIGN PATENT DOCUMENTS 2424733  1/1980  France .............................. 128/663

OTHER PUBLICATIONS

McCormock, T. et al., "Doppler Ultrasound Probe for Assessment of Blood Flow in Oesophogeal Varices", The Lovcet, Mar. 26, 1983.

Hisanaga, K. et al., "A New Trans-Digestive Tract Scanner with a Gastro-Fiber-Scope", Proc. 23rd AIUM 1978, p. 170.

Baba, K. "UTS Diagnostic Apparatus", Europ. Pat. Appln. Publ. No. 0065275 published 24-11-82.

Webster, W., "Catheter for Removing Plaque", PCT US84/00474 publ., No. WO85/00510 published 14 Feb. 1985.

Wilson, R. F. et al., "Transluminal Subselective Measurement of Coronary Artery Blood Flow Velocity and Vasodilator Reserve in Man", Circulation, V. 72, pp. 82-92 (Jul. 1985).

White, C. W. et al., "Does Visual Interpretation of the Cornary Arteriogram Predict the Physiologic Importance of a Cornary Stenosis?", 310NEJM 819-824, (Mar. 1984).

Cole, J. S. et al., "The Pulsed Doppler Coronary Artery Catheter", vol. 56, Circulation, pp. 18-25 (Jul. 1977).

Bevchimol, A. et al., "Aortic Flow Velocity in Man During Cardiac Arrythmias Measured with the Doppler Catheter-Flowmeter System"; 78, Amer. Hrt. Jrnl. pp. 649-659 (Nov. 1969).

Laenger, C. J. et al., "Development of Special Purpose Catheter Tip Transducers", (Aug. 1967) (unpublished manuscript).

(List continued on next page.)

Primary Examiner—Francis J. Jaworski
Attorney, Agent, or Firm—Arnold, White & Durkee

[57] ABSTRACT

An invasive, fluid velocity measuring wire guide particularly adapted and of a size (less than 0.030 inch) for subselective placement in the coronary arterial tree, which includes a Doppler mechanism for determining the blood flow velocity in the region of the distal end of the wire guide. Although the wire guide is particularly adapted for diagnosing coronary arterial disease subselectively; it is of such a size and manipulability to be useful in other blood flow and biological fluid flow analyses. Preferably, the wire guide if flexible and steerable for precise placement. The wire guide includes an elongated wire member having a Doppler crystal attached in longitudinal alignment at its distal end. Electrical leads extend from the Doppler crystal along the wire member to the appropriate test equipment for measuring the fluid flow velocity in the region of the Doppler crystal.

24 Claims, 2 Drawing Sheets

OTHER PUBLICATIONS

Hartley, C. J., "An UTS Pulsed Doppler System for Measuring Blood Flow in Small Animals", 37 J. Appl. Physiology, pp. 626-629, (Oct. 1974).

Martin, R. W. et al., "UTS Catheter-Tip Instrument for Measurement of Vessel Cross-Sectional Area", unpublished paper presented at the 27th Annual Conf. on Engineering in Med & Biol. (Oct. 1974).

Hartley, C. J. et al., "A Single-Crystal UTS Catheter-Tip Velocity Probe", Med. Instr. V. 8, pp. 241-243 (1974).

Neoleigh, R. C. et al., "A Venous Pulse Doppler Catheter-Tip Flowmeter for Measuring Arterial Blood Velocity, Flow & Diameter", 12th Ann. Rocky Mtn. Bioeng. Symp., Denver, Colo., Apr. 28-30, 1975.

Coppess, M. A. et al., "An Ultrasonic Pulsed Doppler Balloon Catheter for Use in Cardiovascular Diagnosis", vol. 19, Biol. Med. Sci Instr., 9-16 (1983).

Neoleigh, R. C. et al., "A Venous Pulse Doppler Catheter-Tip Flowmeter for Measuring Arterial BV, BF & Diameter in Deep Arteries", 15 ISA Trans. 84-87 (1976).

Martin, R. W. et al., "An UTS Catheter for Intravascular Measurement of Blood Flow: Technical Details, Trans. on Sonics & Ultrasonics, vol. SU-27, No. 6 (Nov. 1983).

DOPPLER TIP WIRE GUIDE

This is a continuation of application Ser. No. 888,060 filed July 18, 1986, now abandoned.

BACKGROUND OF THE INVENTION

1. Field of the Invention

This invention relates to wire guides having a Doppler mechanism for determining in vivo flow velocity of a biological fluid. In particular, it relates to a flexible, steerable, fluid velocity measuring wire guide which is receivable in a catheter and positionable subselectively in the coronary arterial tree for diagnosing heart disease.

2. Description of the Related Art

Coronary artery disease is a common medical problem, particularly in the U.S., and often manifests itself as a constriction of stenosis in the arterial tree. Coronary artery disease can lead to increased arterial stenosis and gradual diminution of reactive hypermic response. Because arterial disease is commonplace, it is important to properly diagnose the presence of specific lesions or vessel stenosis and to properly evaluate the efficacy of treatment of these arterial lesions.

Stenosis past the coronary ostium are not only difficult to identify and treat, but are also prime concern because of their effect on available coronary vasodilator reserve. To identify coronary disease, the arteriogram has long been used to determine the presence and extent of stenoses. Applicant's co-pending application Ser. No. 775,857 (incorporated herein by reference) discusses the inadequacies of the arteriogram as an indication of the presence and nature of coronary artery disease. See, White, et al., *Interpretation of the Arteriogram*, 310 New Eng. J. Med. 819-824, (1984).

Transluminal angiplasty (enlargement of the lumen of a stenotic vessel using an intravascular catether) was initiated by Dotter and Judkins in the mid-1960's. However, prior to the work of Gruentzig (mid-1970's), coronary stenoses were usually treated by open heart surgery, such as coronary artery bypass surgery. Gruentzig developed an inflatable non-elastomeric balloon mounted on a small catheter which could be introduced into the vessel across the stenoses, and then inflated with a sufficient force to enlarge the stenotic lumen. Since the pioneering work of Gruentzig in the mid-1970's, there have been significant improvements in the equipment and techniques developed for this percutaneous transluminal coronary angioplasty (PTCA) procedure. In the United States, the growth in the number of PYCA procedures being performed has been dramatic—approximately 1,000 PTCA procedures were performed in 1980 and over 100,000 procedures were performed in 1986. PTCA procedures represent a major alternative to bypass surgery and have enjoyed an increasing success rate.

Although PTCA procedures have become increasingly successful, a major cause of failures is the inability to accurately identify the regions of stenoses and to evaluate the success of the angioplasty across the stenotic vessel. That is, the arteriogram is still the prime method of identifying and evaluating the stenosis and can lead to any number of mistakes in interpretations—such as observer error, superselective injection, pulsatile injection of contrast media, total occlusion, etc. Further, angiogrpahic evaluation of the region of stenoses after the PTCA procedure is often difficult, owing to the poor defination of the vessel after angioplasty. Thus, while such coronary angioplasty techniques have been relatively successful in treating the regions of stenosis, the unreliability of the arteriogram has been a significant detraction from the efficiency of angioplasty.

Because a PTCA procedure uses a steerable guidewire to place the angioplasty balloon catheter subselectively in the coronary vessels, it would be a significant advance in the art and a major improvement over the arteriogram if a guidewire were devised which was capable of getting a direct indication of blood flow in a particular region of the coronary vessel. Further, it would be a significant advance if such a guidewire capable of measuring fluid velocity were devised which was useful in measuring velocity of other biological fluids and was easily positioned in a biological vessel of interest.

SUMMARY OF THE INVENTION

The velocity determining wire guide of the present invention provides one solution for subselectively identifying the nature and extent of coronary artery disease, and further provides a device which is useful in invasively determining biological fluid flow in any small or constricted vessel. Advantageously, the wire guide of the present invention is of such a size (less than 0.030 inch) that it will easily fit down the central lumen or side channel of an angioplasty catheter which itself is such a size to be subselectively in the coronary arterial tree. Preferably, the wire guide hereof is steerable and is useful not only as a probe for locating regions of heart disease, but also as a guide for an angioplasty catheter.

Broadly speaking, the wire guide of the present invention includes an elongated member which is generally longitudinally inelastic and flexible for threading engagement with the catheter. A Doppler mechanism is coupled to the distal end of the elongated member and is operable for determining the velocity of the blood when inserted in the arterial tree. Electrical lead means coupled to the Doppler mechanism run along the member towards the proximal end of the guide wire, such that blood velocity can be determined as the wire guide is selectively advanced in the arterial tree.

In a preferred form, the wire guide includes an elongated support wire having a pair of electrical leads running along the length thereof, with the leads and support wire encapsulated in an insulator sheath. A Doppler crystal is connected to the leads and is secured to the distal end of the sheath with the face of the Doppler crystal generally perpendicular to the longitudinal axis of the sheath. In an alternative embodiment, the distal end of the wire guide is bent at a small angle, such that torque control of the support wire reorients the distal end carrying the Doppler crsytal for selective steerability and better Doppler signal reception.

In another preferred embodiment, the elongated member comprises a helically wound spring coil defining a central passageway therein. The Doppler crystal is fitted to the distal end of the spring coil and electrical leads are coupled to the Doppler crystal and received within the central passageway. An elongated inelastic fixed core wire is secured to the distal end and proximal end of the spring coil to prevent longitudinal elongation of the spring coil. In an alternative embodiment, the distal portion of the spring coil is in a "J" shaped configuration. Advantageously, a movable coil wire is shiftably received in the central passageway and operable such that when it is shifted into the region of the "J"

shaped configuration, the region tends to straighten out. Thus, the movable core allows the Doppler crystal to be oriented as desired and allows the distal end of the spring coil to be directionally aligned for subselective movement in the arterial tree.

DESCRIPTION OF THE PREFERRED EMBODIMENT

Turning now to the drawings, a wire guide 10 in accordance with the present invention is illustrated in various embodiments. Broadly speaking, the wire guide 10 includes an elongated, flexible, longitudinally inelastic wire member 12, Doppler mechanism 14 and electrical leads 16 running the length of the member 12.

In more detail, in the embodiments depicted in FIGS. 1-4 the wire member 12 includes an elongated support wire 20 which is flexible and longitudinally inelastic, and torquable in the sense that a twisting moment at the proximal end will impart a twisting moment at the distal end. The support wire 20 is preferably a stainless steel piano wire and in the preferred embodiment, has an approximate outer diameter of 0.012 inches. The electrical lead 16 comprises a pair of electrical connector wires juxtaposed in adjoining relationship to the support wire 20. The leads 16 have an approximate outer diameter of 0.002 inches and preferably include a copper conductor having four layers of a thin nylon insulation. A cylindrical, insulator sheath 22 of plastic, nylon, polyurethane, or other suitable insulating material envelopes the support wire 20 and electrical leads 16, to present an outer diameter preferably less than 0.030 inches, and in the preferred embodiment having an outer diameter of 0.019 inches.

Figure 1:
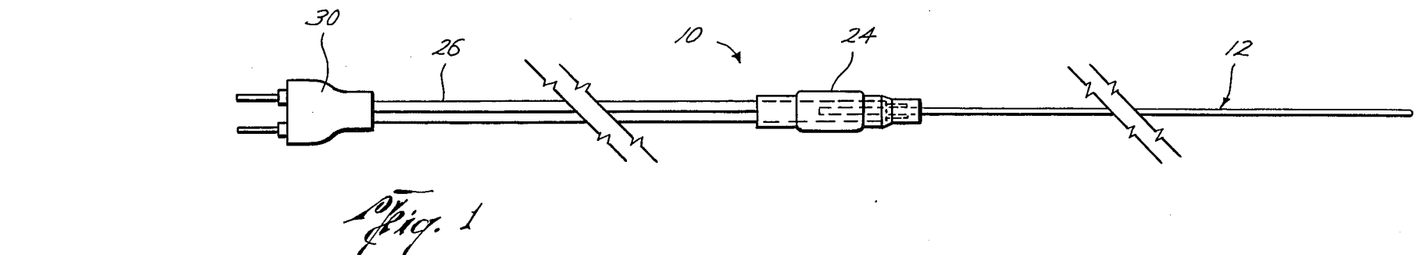
FIG. 1 illustrates a fragmentary, side elevational view of a velocity measuring wire guide in accordance with the present invention.
Figures 2, 3, 4:
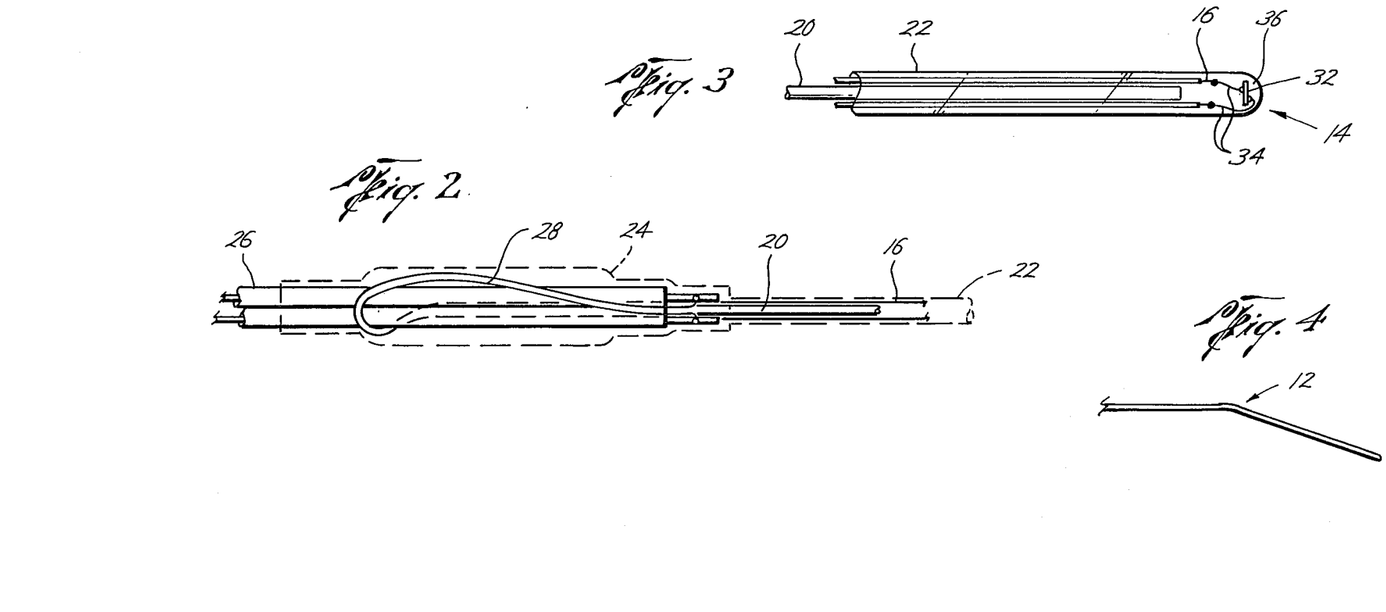
FIG. 2 is an enlarged, fragmentary, sectional view of a proximal portion of the wire guide illustrated in FIG. 1.
FIG. 3 is an enlarged, fragmentary, sectional view of the distal region of the wire guide of FIG. 1.
FIG. 4 is a fragmentary, side elevational view of an alternative embodiment of the distal region of the wire guide of FIG. 1.

Turning to FIG. 2, the sheath 22 is received in an insulating sleeve 24 substantially as shown. Doppler connector cable 26 leads into the opposite end of the sleeve 24 and is connected to the lead 16 by the coupling wires 28 as shown. As illustrated in FIG. 1, the connector cable 26 terminates in a universal coupling 30.

As shown in detail in FIG. 3, the Doppler mechanism 14 includes a generally flat Doppler crystal 32 which is preferably a piezoelectric ceramic crystal comprising a lead-zircanate-titanate material. The Doppler crystal 32 is approximatley 0.003 inch in thickness and is designed to resonate at 20 megahertz. A pair of conductors (preferably gold) are attached to the crystal 32 such that the Doppler crystal 32 operates as a pulsed Doppler, operating alternatively as a transmitter and receiver. The conductors 34 are connected by the electromechanical joints to the leads 16. A potting compound 36, such as an epoxy resin, secures the Doppler crystal 32 in the circular opening defined by the sheath 22. As can be seen in FIG. 3, the distal end of the support wire 20 terminates prior to the distal end of the sheath 22, leaving a void which is filled by the potting compound 36.

As can be appreciated by those skilled in the art, Doppler mechanism 14 is connected through the universal coupling 30 to operate as an ultrasonic pulsed Doppler device capable of measuring the velocity of a fluid. See e.g., C. Hartley and J. Cole, *Pulsed Doppler Flow Measurement*, 37 J. App. Phys., 626–629 (1974) (incorporated herein by reference).

Comparing FIGS. 1 and 4, it is seen that FIG. 4 presents a slightly different embodiment in which the distal region of the wire guide 10 (FIG. 4) is bent at a slight angle relative to the remaining longitudinal alignment of the member 12. Thus, the embodiment of FIGS. 1-3 presents a "straight" wire guide while the FIG. 4 embodiment has a "hockey stick" orientation of its distal region. In some applications, the FIG. 4 embodiment allows better steerability (torquing the member 12) to orient the distal end towards the coronary vessel of interest.

Turning now to FIGS. 5-8, further embodiments of the distal region of the wire guide 10 in accordance with the present invention are illustrated. In the FIG. 5-8 embodiments, the member 12 comprises a helically wound spring coil 40 having an annular cross section to define a central passageway 42. The outer diameter of the spring coil 40 is preferably less than 0.030 inches and as illustrated, is less than 0.019 inch, such that the wire guide 10 will easily fit in the lumen or coupling channel of a dilation catheter or the like. An elongated fixed core wire 44 is coupled to the spring coil 40 at the distal and proximal ends to prevent longitudinal elongation of the weld 46 securing the fixed core 44 to the last two winds of the spring coil 40 at the distal end of the wire guide 10, it being understood that the fixed core 44 is similar secured to the proximal end.

Figures 5, 6:
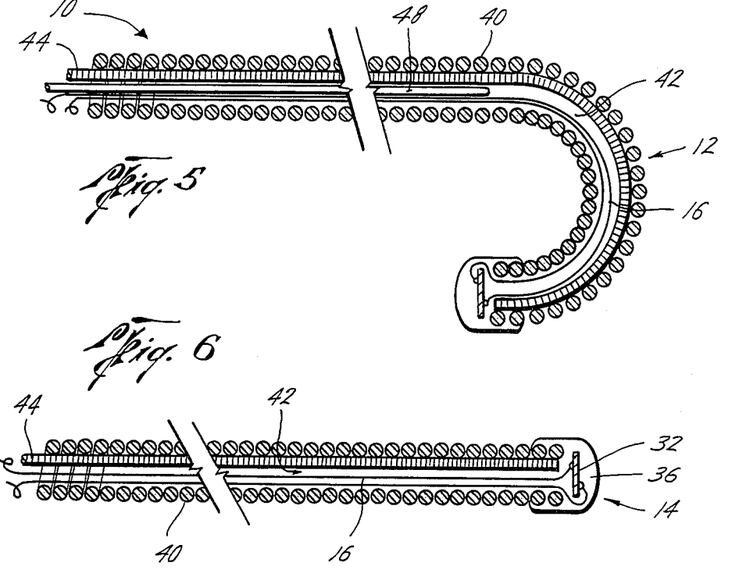
FIG. 5 is an enlarged, fragmentary, sectional view of a wire guide in accordance with the present invention which includes a coil spring in a "J" shaped configuration and a movable core.
FIG. 6 is an enlarged, fragmentary, sectional view of a wire guide which includes a straight coil spring.
Figure 8:
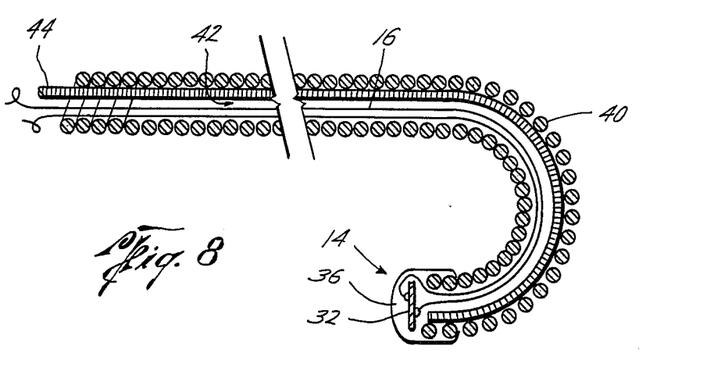
FIG. 8 is an enlarged, fragmentary, sectional view of a wire guide in accordance with the present invention having a "J" shaped distal region without a moveable core.

In the embodiments of FIGS. 5 and 8, the distal region of the wire guide 10 is made to assume a "J" shaped configuration in its normal static state. While an introducer (not shown) is commonly used to straighten the "J" shaped configuration during percutaneous insertion, the embodiment of FIG. 5 additionally includes an elongated movable core 48 shiftably received in the central passageway 42. As those skilled in the art will appreciate, the movable core 48 is usually not flexible enough to conform to the "J" shaped configuration of the central passageway 42. Rather, the movable core 48 as it is advanced to the distal region towards a more rectilinear orientation. The degree of advancement of the movable core 48 towards the distal end determines the degree of movement of the distal region from a "J" shaped configuration towards a rectilinear orientation. Typically, the movable core 48 is somewhat flexible, such that even with the movable core 48 fully inserted in the central passageway 42, the distal end still presents some angularity (see e.g. FIG. 4).

The Doppler mechanism 14 includes the Doppler crystal 32 secured in place by a potting compound 36 to the distal end of the spring coil 40. In the embodiments of FIGS. 5-8 the potting compound 36 not only secures the crystal 32 to the spring coil 40, but additionally occupies a portion of the central passageway 42 to effect a seal. It should be appreciated, however, that a Doppler crystal 32 can be donut-shaped and the potting compound 36 partially selectively removed to place the central passageway 42 in communication with the blood stream or other biological fluid. Such an alteration would allow the introduction of chemicals or fluids into the blood stream, for example angiogram dye, through the wire guide 10.

The electrical leads 16 are connected to the Doppler crystal 32 in similar fashion as the connections made in the embodiment of FIGS. 1-4. In the embodiments of FIGS. 5-8, the leads 16 are disposed in the central passageway 42 and coupled to a connector cable or similar device leading to an ultrasonic Doppler flow monitor.

Figure 7:
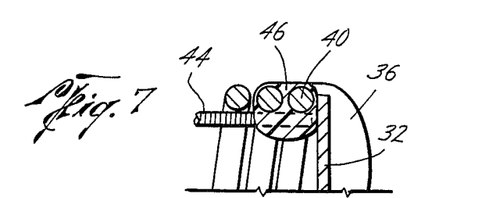
FIG. 7 is an enlarged, fragmentary, sectional view showing in detail the joinder of the Doppler crystal to the coil spring.

The embodiments of FIGS. 5, 6 and 8 differ in only minor detail. FIG. 7 shows a cross-sectional view of the distal end of the member 12 common to the FIG. 5, 6 and 8 embodiments. As should be readily apparent from the drawings, FIG. 6 shows an embodiment in which the distal region of the wire guide is "straight," while FIGS. 5 and 8 show embodiments in which the distal region is in the "J" shaped configuration. In FIG. 5 a movable core 48 is included, while FIG. 8 only a fixed core 44 is contemplated.

Use

While the wire guide 10 in accordance with the present invention will undoubtedly find utility in a wide variety of medical applications as a diagnostic tool, it is anticipated that wire guide 10 may be particularly advantageously used in PTCA procedures. In a typical PTCA procedure, either a femoral or brachial approach is taken, using a standard percutaneous procedure such as the Seldinger approach. In most angioplasty procedures, a right heart catheter is inserted to monitor baseline filling pressures and ventricular pacing. Such right heart diagnostic catheterization is relatively easy using a balloon-tip, flow directed catheter (e.g. Swan-Ganz catheter, Edwards Laboratory, Santa Ana, Calif.), in view of the less stringent dimensional restrictions of the pulmonary artery.

Manipulating the catheters and guidewire subselectively past the ostium to perform the angioplasty is often a diffiuclt procedure. In most PTCA procedures, a guiding catheter, balloon dilation catheter, and a steerable guide wire are used. The guiding catheter is usually positioned in the ostium of the coronary artery with the dilation catheter positioned within the guiding catheter for advancement over the guidewire. Most dilating catheters have a central lumen for the sliding reception of the guidewire, while some catheters may have an elongated open side channel for engaging the guidewire. The guidewire is specially designed to combine tip softness, radiographic visability, and precise torque control so that it can be positioned throughout the sometimes tortuous arterial tree and stenotic regions. Because the dilating catheter typically has a small lumen or channel, the guidewires normally have a diameter less than 0.020 inches.

In the common PTCA procedure, baseline angiograms are used for identifying the regions of stenosis and for positioning the guiding catheter and dilating catheter. The dilating catheter and the guidewire are successively advanced through the target stenoses and positioned relative to the lesions for evaluating by a series of contrast injections through either the guiding catheter or dilation catheter. Thus, the guidewire serves as a track which permits safe advancement of the dilation catheter through the region of the stenoses. Once the dilating catheter is positioned, it is successfully inflated (sometimes with varying pressures) until the operator believes that the stenosis have been reduced. As previously indicated, after dilation, the stenosis is typically angiographically evaluated and this evaluation has proven to be somewhat deficient.

Turning to use of the wire guide 10 in accordance with the present invention, the embodiments of FIGS. 4, 5 and 8, represent wire guide configurations which offer the best steerability. However, all of the embodiments illustrated in the drawing are positionable by torque, and hence steerable. In the preferred procedure, a steerable wire guide 10 is inserted into the vessel and the dilating catheter inserted into the vessel in operable engagement with the wire guide 10. The wire guide 10 is manipulated past the ostium subselectively into the coronary artery of interest. Typically, an injection of contrast media would be made through the dilation catheter or guiding catheter to verify the position of wire guide 10.

The dilating catheter is shifted sequentially to follow the wire guide 10 into the target stenotic region. Particularly in the embodiment of FIG. 5, the movable core 48 is positioned in the central passageway 42 to orient the distal end of the wire guide 10 to a desired angularity. The member 12 is then torqued to twist the distal end of the wire guide 10 towards the target artery and the wire guide 10 is then advanced into the artery.

It is readily appreciated that while the wire guide 10 is being advanced, the Doppler crystal 32 is taking continuous readings giving the operator an indication of the blood flow velocity in the region of the distal end of the wire guide 10. Advantageously, this constant indication of blood velocity—and hence blood flow—not only aids in positioning the wire guide 10, but also is of great value in determining the efficacy of the PTCA procedure by giving an immediacy of measurement. That is, after the dilating catheter is positioned across the region of the target stenosis and inflated, the operator has a constant indication of a blood flow across the stenosis before angioplasty and after each successive inflation. Thus, the wire guide 10 in accordance with the present invention represents a substantial advance in the art as a tool for identifying and evaluating coronary disease, particularly in evaluating the efficacy of a PTCA procedure.

As an alternative to the preferred method, the wire guide 10 in accordance with the present invention (particularly the embodiments of FIGS. 1 and 6) is useful in conjunction with conventional wire guides currently used in angioplasty. In the alternative method, a conventional wire guide is positioned using standard angiogram techniques and the dilating balloon catheter advanced into the target stenotic region. The conventional wire guide is then removed and the wire guide 10 in accordance with the present invention inserted through the central lumen (or along the side channel) of the balloon catheter. Thus, the wire guide 10 is used primarily as a tool for evaluating the efficacy of the angioplasty, and is not used in the positioning process.

Those skilled in the art will also appreciate that the wire guide in accordance with the present invention has many other in vivo uses outside of the PTCA procedure. It is readily apparent that because of its small size, flexibility, and steerbility, the wire guide 10 can function effectively as a diagnostic probe in evaluating blood flow or other biological fluid flow throughout the body.

I claim:

1. A blood velocity measuring wire guide adapted for operative coupling to a catheter, the wire guide comprising:
    an elongated flexible support wire having distal and proximal ends which is generally longitudinally inelastic and flexible for threaded engagement with the catheter;
    Doppler means including a Doppler crystal mounted to the distal end of said wire for determining the velocity of the blood with the wire guide inserted in a blood vessel; and
    electrical lead means operatively coupled to the Doppler means and coupled to said wire along its length.

2. The wire guide according to claim 1, including an elongated insulator sheath surrounding the support wire and lead means, the sheath having a distal end.

3. The wire guide according to claim 2, the Doppler means including a pair of electrical connectors operatively coupled to said Doppler crystal and to said lead means.

4. The wire guide according to claim 2, the distal end of the sheath defining an opening, said Doppler means including a potting compound securing the Doppler crystal in the opening.

5. The wire guide according to claim 4, said sheath distal end extending past the distal end of the support wire, said potting compound extending from the sheath distal end into adjoining relation with said support wire.

6. The wire guide according to claim 2, including an insulating sleeve and a connector cable, said proximal end of said wire being received in the insulating sleeve, said lead means being coupled to the connector cable extending into the sleeve.

7. The wire guide according to claim 1, the elongated support wire comprising a helically wound spring coil defining a central passageway.

8. The wire guide according to claim 7, said lead means extending through said central passageway.

9. The wire guide according to claim 7, the spring coil comprising a plurality of interconnected winds, the two winds adjacent the distal end being laterally secured to each other.

10. The wire guide according to claim 7, including an elongated fixed core wire secured to the spring coil at the proximal and distal ends of the spring coil to prevent elongation of the spring coil.

11. The wire guide according to claim 7, said spring coil presenting a distal end having a flexible "J" shaped configuration in its unstressed, static state.

12. The wire guide according to claim 11, including an elongated movable core wire received in said central passgeway and operable when shifted into the distal end to straighten the "J" shaped configuration towards a rectilinear orientation.

13. The wire guide according to claim 7, the Doppler means comprising a Doppler crystal secured by a potting compound to the distal end of the spring coil.

14. The wire guide according to claim 1, the outer diameter of said member being less than 0.030 inch.

15. A fluid velocity measuring wire guide comprising:
    an elongated support wire which is generally inelastic and incompressible;
    a pair of electrical leads extending along the length of said support wire;
    an elongated insulator sheath surrounding the support wire and leads and having an outer diameter less than 0.030 inch;
    Doppler means for measuring the velocity of a fluid, including,
        a Doppler crystal coupled to the distal end of the sheath and operatively coupled to the electrical leads, such that with the Doppler crystal immersed in a fluid, the wire guide is operable for determining the velocity of the fluid.

16. The wire guide according to claim 15, the support wire having a distal end which terminates prior to said Doppler crystal.

17. The wire guide according to claim 15, the Doppler crystal being coupled to the sheath by a potting compound and having a flat transmission and reception face which is oriented axially relative to the distal end of the sheath.

18. A fluid velocity measuring wire guide comprising:
    an elongated, flexible, helically wound spring coil defining a central passageway and having an outer diameter less than 0.030 inch;
    an elongated, inelastic, flexible fixed core wire secured to the distal and proximal ends of the spring coil to prevent elongation of the spring coil;
    Doppler means for determining the velocity of a fluid when immersed therein, including a Doppler crystal mounted to the distal end of the spring coil and electrical leads coupled to the Doppler crystal and received in said central passageway.

19. The wire guide according to claim 18, the region of spring coil proximate the Doppler crystal presenting a "J" shaped configuration in its unstressed, static state.

20. The wire guide according to claim 19, including an elongated, movable core shiftably received in the central passageway and operable for straightening said "J" shaped region towards a rectilinear configuration.

21. The wire guide according to claim 18, the spring coil being generally cylindrical in cross-section and the Doppler crystal having a generally flat transmission and reception face oriented generally axially relative to the cylindrical spring coil.

22. A method of determining the blood flow velocity subselectively in the coronary arterial tree comprising the steps of:
    inserting percutaneously a Doppler wire guide having a Doppler crystal coupled to its distal end into a blood vessel;
    inserting percutaneously a catheter into the blood vessel, the catheter and wire guide being in operable engagement for following the same path of travel in the blood vessel;
    manipulating the Doppler wire guide through the blood vessel;
    positioning the Doppler wire guide and catheter in a region of interest in the blood vessel; and
    measuring the blood flow velocity in said region with said Doppler wire guide operatively engaging said catheter including the substep of operating the Doppler means for determining blood velocity.

23. The method according to claim 22, including the steps of inserting a positioning wire guide into the blood vesssel and into the region of interest and shifting the catheter sequentially to follow the positioning wire guide.

24. The method according to claim 23, including the steps of:

withdrawing said positioning wire guide from said catheter after the catheter is positioned in the region of interest; and inserting the Doppler wire guide into said catheter after withdrawing the positioning wire guide, with the Doppler means located generally in region of interest.

* * * * *

UNITED STATES PATENT AND TRADEMARK OFFICE
CERTIFICATE OF CORRECTION

PATENT NO. : 4,771,788

DATED : September 20, 1988

INVENTOR(S) : Huntly D. Millar

It is certified that error appears in the above-identified patent and that said Letters Patent is hereby corrected as shown below:

In the ABSTRACT, line 10, please delete "if" and insert therefor -- is --.

In Column 1, line 21, please delete "hypermic" and insert therefor -- hyperemic --.

In Column 1, line 27, please insert -- of -- between the words "also" and "prime".

In Column 1, line 37, please delete "angiplasty" and insert therefor -- angioplasty --.

In Column 1, line 52, please delete "PYCA" and insert therefor -- PTCA --.

In Column 1, line 67, please delete "angiogrpahic" and insert therefor -- angiographic --.

In Column 2, line 1, please delete "defination" and insert therefor -- definition --.

In Column 2, line 29, please delete "subselectively" and insert therefor -- subselective --.

In Column 2, line 54, please delete "crsytal" and insert therefor -- crystal --.

In Column 4, line 2, please delete "lead-zircanate-titanate" and insert therefor -- lead-zirconate-titanate --.

In Column 4, line 44, after the words "elongation of" please insert -- the spring coil 40 during manipulation. FIG 7 shows --.

In Column 4, line 60, after the words "to the" please insert the words -- distal end of the member 12, tends to straighten the --

In Column 6, line 9, please delete "have" and insert -- has --.

UNITED STATES PATENT AND TRADEMARK OFFICE
CERTIFICATE OF CORRECTION

PATENT NO. : 4,771,788

DATED : September 20, 1988

INVENTOR(S) : Huntly D. Miller

It is certified that error appears in the above-identified patent and that said Letters Patent is hereby corrected as shown below:

In Column 7, line 3, delete "steerbility" and insert therefor

-- steerability --.

Signed and Sealed this

Twenty-eighth Day of February, 1989

*Attest:*

DONALD J. QUIGG

*Attesting Officer*  *Commissioner of Patents and Trademarks*